United States Patent [19]

Collin et al.

[11] Patent Number: 5,667,789

[45] Date of Patent: Sep. 16, 1997

[54] SALICYLIC ACID DERIVATIVE AS A STABILIZER FOR AN OIL-IN-WATER EMULSION

[75] Inventors: Nathalie Collin, Sceaux; Eric Quemin, Villepinte; Didier Candau, Bievres, all of France

[73] Assignee: L'Oreal, Paris, France

[21] Appl. No.: 552,934

[22] Filed: Nov. 3, 1995

[30] Foreign Application Priority Data

Nov. 3, 1994 [FR] France .................................. 94 13127

[51] Int. Cl.⁶ ...................................................... A61K 7/48
[52] U.S. Cl. ........................ 424/401; 514/159; 514/844; 514/859; 514/937
[58] Field of Search ........................... 424/401; 514/159, 514/844, 859, 937

[56] References Cited

U.S. PATENT DOCUMENTS

| | | | |
|---|---|---|---|
| 5,001,156 | 3/1991 | Philippe et al. | 514/555 |
| 5,137,923 | 8/1992 | Philippe et al. | 514/859 |
| 5,411,742 | 5/1995 | Sebag et al. | 424/450 |

FOREIGN PATENT DOCUMENTS

| | | |
|---|---|---|
| A-0 378 936 | 7/1990 | European Pat. Off. . |
| A-0 570 230 | 11/1993 | European Pat. Off. . |
| A-0 585 170 | 3/1994 | European Pat. Off. . |
| A-0 616 799 | 9/1994 | European Pat. Off. . |
| A-2 607 498 | 6/1988 | France . |
| A-2 174 906 | 11/1986 | United Kingdom . |

*Primary Examiner*—Jyothsan Venkat
*Attorney, Agent, or Firm*—Oblon, Spivak, McClelland, Maier & Neustadt, P.C.

[57] ABSTRACT

The invention relates to the use of a salicylic acid derivative salified with a base, as a stabilizer for an oil-in-water emulsion. This salified derivative has the same properties as its acidic homologue, while at the same time having a less irritating nature. This salified derivative is, in particular, an n-alkanoyl-5-salicylic acid salified with an amphoteric base such as lysine or arginine. The present compositions are more especially intended for the cosmetic and dermatological fields.

23 Claims, No Drawings

SALICYLIC ACID DERIVATIVE AS A STABILIZER FOR AN OIL-IN-WATER EMULSION

BACKGROUND OF THE INVENTION

1. Field of the Invention

The present invention relates to the use of salicylic acid derivatives as stabilizers for oil-in-water emulsions, as well as to cosmetic and/or dermatological emulsions containing such a derivative. The present emulsions are intended in particular for the treatment or care of the skin, both of the human face and body, including the scalp and the nails, and even more especially for treating and/or combating acne, greasy skin with a tendency towards acne, and the ageing (wrinkles, fine lines, complexion) and pigmentation of the skin.

2. Discussion of the Background

It is known to use salicylic acid derivatives as keratolytic agents for treating acne and as an anti-ageing agent in cosmetic and/or dermatological compositions (see FR-A-2,581,542 and EP-A-378,936).

These derivatives are of great value, given their biological effects on the skin. They make it possible in particular to impart a light and radiant complexion to the face, and thus a healthy look and a smooth and younger appearance, as well as making it possible to remove comedones caused by acne.

However, their use poses a problem insofar as they are in crystalline form and insofar as they are soluble neither in water nor in the oils traditionally used in the cosmetic and dermatological fields, such as mineral oils (petrolatum, paraffin).

Thus, if they are introduced as they are into cosmetic and/or dermatological compositions, they remain in the form of crystals, thereby making the use of the composition containing them inefficient for treating the skin.

On the other hand, these derivatives are soluble in lower alcohols such as ethanol or isopropanol, Guerbet alcohols or in solvents such as octyldodecanol, certain glycols, short-chain (<C12) fatty alcohols, which are polyoxyethylenated or polyoxypropylenated, or alternatively short-chain (<C12) esters.

The lower alcohols have the drawback of drying and irritating the skin; they are poorly tolerated by sensitive or fragile skin, especially in repeated applications. It is thus preferred to avoid using them in body- and/or face-care products.

Moreover, the short-chain fatty alcohols and fatty esters, as well as certain glycols, make it possible to solubilize these derivatives, leading to the deep-down penetration of active agents into the skin, which is not necessarily desirable for care products.

Currently, it is increasingly sought generally to limit the use of solvents in skin-care products, since these solvents are not always well tolerated and may lead to irritation when they are used in too large an amount.

The inventors have thus sought to formulate the salicylic acid derivatives in compositions containing the least possible amount of solvents.

Moreover, these derivatives have the major drawback of causing stinging, itching and pulling sensations after their application, which may lead to a level of discomfort such that their use by individuals with sensitive skin is often prevented. This discomfort is due in particular to the acidic functional group of these derivatives.

Thus, there is a need for cosmetic and/or dermatological compositions based on a salicylic acid derivative, which imparts a healthy look and rejuvenation to the skin and also removes comedones, without resulting in the above-mentioned drawbacks.

SUMMARY OF THE INVENTION

Accordingly, it is one object of the present method to provide novel cosmetic and/or dermatological compositions.

It is another object of the present invention to provide novel cosmetic and/or dermatological compositions which contain a salicylic acid derivative.

It is another object of the present invention to provide novel cosmetic and/or dermatological compositions which contain a salicylic acid derivative but exhibit a reduced tendency to irritate the skin.

It is another object of the present invention to provide novel cosmetic and/or dermatological compositions which contain a salicylic acid derivative and which contain a reduced amount or even no additional emulsifying agent.

It is another object of the present invention to provide novel cosmetic and/or dermatological compositions which contain a salicylic acid derivative and which contain a reduced amount or even no organic solvent.

It is another object of the present invention to provide novel cosmetic and/or dermatological compositions which contain a salicylic acid derivative and which are useful for preventing and/or combating ache and/or greasy skin and/or the ageing and/or pigmentation of the skin.

It is another object of the present invention to provide a method of stabilizing an emulsion of an oily phase and an aqueous phase in which the emulsion contains a salicylic acid derivative and contains a reduced amount of or even no additional emulsifying agent.

It is another object of the present invention to provide a novel method for preventing and/or combating acne and/or greasy skin and/or the ageing and/or pigmentation of skin.

These and other objects, which will become apparent during the following detailed description, have been achieved by the inventors' discovery that salicylic acid derivatives can be introduced in salified form into cosmetic and/or dermatological compositions, without these derivatives recrystallizing and without it being necessary to use a large amount of solvent. The inventors have found, surprisingly, that it is possible to stabilize oil-in-water emulsions with salts of salicylic acid derivatives, making it possible to dispense with the use of irritating lipophilic solvents, without being inconvenienced by recrystallization of these salicylic acid derivatives.

Thus, the salified salicylic acid derivative(s) lie at the oil-water interface and surround the oil droplets and stabilize the obtained emulsion without use of an emulsifying agent.

More precisely, the subject of the present invention is the use of at least one salicylic acid derivative salified with a base, as a dispersing agent of an oily phase in an aqueous phase to obtain an oil-in-water emulsion free of emulsifying agent.

These salified salicylic acid derivatives also have the advantage of being less aggressive than their acidic counterparts, while at the same time having comparable properties.

DETAILED DESCRIPTION OF THE PREFERRED EMBODIMENTS

In particular, the salicylic acid derivatives to which the present invention applies have the following formula (I):

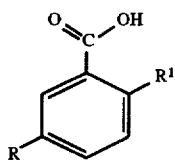

in which:

R represents a saturated, linear, branched, or cyclic aliphatic, alkoxy, alkanoyloxy, alkanoyl, or alkyl carboxy group, each group having 2 to 22 carbon atoms and each group optionally substituted with at least one substituent selected from the group consisting of halogen, trifluoromethyl, hydroxyl, hydroxyl esterified with a carboxylic acid having 1 to 6 carbon atoms, carboxyl, and carboxyl esterified with a lower alcohol having 1 to 6 carbon atoms; or an unsaturated, linear, branched, or cyclic alkenyl, alkenyloxy, alkenoyloxy, alkenoyl, or alkenyl carboxy group having one or more conjugated or non-conjugated double bonds, each group having 2 to 22 carbon atoms and each group optionally substituted with at least one substituent selected from the group consisting of halogen, trifluoromethyl, hydroxyl, hydroxyl esterified with an carboxylic acid having 1 to 6 carbon atoms, carboxyl, and carboxyl esterified with a lower alcohol having 1 to 6 carbon atoms;

R' represents a hydroxyl group or an ester function of formula:

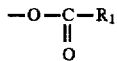

where $R_1$ is a saturated or unsaturated aliphatic group having 1 to 18 carbon atoms.

The present emulsions may be used in all the fields using a pharmaceutical form of this type, and especially in the cosmetic and pharmaceutical fields.

Thus, the present invention also provides cosmetic and/or dermatological emulsions containing at least one salified salicylic acid derivative advantageously having the above formula (I) said derivative being at the oil-water interface.

The radical R preferably contains at least 4 carbon atoms. It is formed, for example, of a saturated linear alkyl or alkoxy radical having from 4 to 11 carbon atoms.

The salicylic acid derivative is advantageously chosen from n-octanoyl-5-salicylic acid, n-decanoyl-5-salicylic acid, n-dodecanoyl-5-salicylic acid, n-octyl-5-salicylic acid, n-heptyloxy-5-salicylic acid, and n-heptyloxy-4-salicylic acid, which are salified with a base. It is possible, however, to use the salts of 5-tert-octylsalicylic acid, 3-tert-butyl-5-or 6-methylsalicylic acid, 3,5-diisopropylsalicylic acid, 5-butoxysalicylic acid, or 5-octyloxysalicylic acid. It is also possible to use those described in EP-A-570,230.

As a base capable of salifying the salicylic acid derivative, there may be mentioned inorganic bases such as alkali metal hydroxides (sodium hydroxide and potassium hydroxide) or ammonium hydroxides, or better still organic bases, including mono-, di-, and triethanol amines.

Contrary to the teaching of U.S. Pat. No. 5,091,171, the inventors have found that the salified salicylic acid derivatives have properties comparable to those of the corresponding acidic salicylic acid derivative, irrespective of the base used for the salification (including the alkali metal hydroxides).

Amphoteric bases are preferably used for the salification of the salicylic acid derivatives, that is to say bases having both anionic and cationic functional groups.

The amphoteric bases may be primary, secondary, tertiary or cyclic organic amines, and more especially amino acids. Examples of amphoteric bases which may be mentioned are glycine, lysine, arginine, taurine, histidine, alanine, valine, cysteine, trihydroxymethylaminomethane (TRISTA) and triethanolamine. These bases are used in amounts sufficient to bring the pH of the emulsion to between 5 and 7, and thus close to the pH of the skin. This results in great compatibility between the emulsion of the invention and the skin.

The base is preferably arginine or, better still, lysine. The latter makes it possible to obtain a very fine emulsion which is stable for at least 2 months at room temperature.

Thus, in a preferred embodiment, the present invention also provides cosmetic and/or dermatological emulsions containing at least one salified salicylic acid derivative advantageously having the above formula (I), said derivative being salified by arginine or lysine and being at the oil-water interface.

As examples of a salified salicylic acid derivative which may be used in the invention, there may be mentioned N,N-dimethyl-N-(2-hydroxyethyl)ammonium 5-n-dodecanoylsalicylate, abbreviated to DHADS, hexadecyltrimethylammonium 5-n-octanoylsalicylate and, generally, all the amino derivatives cited in FR-A-2,607,498. It is also possible to use those described in EP-A-36,534.

According to the present invention, the salified salicylic acid derivative or derivatives may be used in an amount sufficient to ensure stabilization of the oil as well as its dispersion in the aqueous phase. In practice, from 0.1% to 10% by weight of the salicylic acid derivative is used based on the total weight of the emulsion, and preferably from 1% to 5% by weight, based on the total weight of the emulsion.

The emulsions of the present invention may contain one or more oils conventionally used in the cosmetic and dermatological fields. In particular, it is possible to use a plant oil (sunflower oil, sweet almond oil, blackcurrant pip oil, or apricot oil), a mineral oil (petrolatum), a silicone-containing oil (cyclomethicone containing 5 or 6 Si-O groups) or a fluoro oil (perfluoropolyether).

One or more polar oils are advantageously used, for example, an oil chosen from Miglyol (caprylic/capric triglycerides) and synthetic oils (Purcellin oil, fatty alcohols, esters or acids such as triglycerides, octyl palmitate or myristate, and hydroxylated, oxyethylenated or oxypropylenated esters or ethers such as isostearyl or myristyl lactate).

The oil or oils of the invention may be used in a proportion of from 10% to 70% by weight, based on the total weight of the emulsion, and preferably from 20% to 40% by weight, based on the total eight of the emulsion.

Typically, the present compositions will contain water in an amount of 29 to 89% by weight, based on the total weight of the emulsion, preferably 25 to 75% by weight, based on the total weight of the emulsion.

It is possible to introduce into the emulsion of the invention one or more other constituents conventionally used in the fields considered, such as antioxidants (vitamin E), preserving agents, opacifying agents, dyes, pigments (titanium oxide or zinc oxide), fragrances, fillers, and also lipophilic adjuvants such as essential oils or essential fatty acids, ceramides, pseudoceramides and glycoceramides. These adjuvants may be present in a total amount of from 0.1% to 15% by weight, based on the total weight of the emulsion.

The emulsion of the present invention may also contain one or more gelling agents such as clays, polysaccharide gums (xanthan), carboxyvinyl polymers or carbomers. These gelling agents are preferably used in an amount ranging from 0.1% to 10% by weight, based on the total weight of the composition.

The emulsions of the present invention may also contain one or more lipophilic or hydrophilic active agents other than the salified salicylic acid derivatives used as stabilizer for the emulsion. These active agents may be moisturizing and/or cicatrizing agents (glycerol and allantoin and the derivatives thereof and compositions containing them), β-hydroxy acids and especially salicylic acid and the non-salified derivatives thereof, α-hydroxy acids such as glycolic acid, tartaric acid, etc., hydrophilic or lipophilic screening agents for screening visible and/or ultraviolet rays, as well as dermatological active agents. These active agents are employed in the amounts conventionally used in the fields considered, and especially in a proportion of from 0.05% to 5% by weight, based on the total weight of the emulsion.

Advantageously, the emulsions of the present invention are free of solvent and/or free of emulsifying agent. This also acts in favor of a quite unaggressive and non-irritating emulsion which is capable of being used by individuals with sensitive skin.

The present emulsion may be prepared by the techniques conventionally used and well-known for the preparation of oil-in-water emulsions.

The salified salicylic acid derivatives used in the present composition may be prepared prior to forming the emulsion by simply neutralizing the salicylic acid derivative with the appropriate base. Alternatively, the salicylic acid derivative may be salified in situ while forming the emulsion by adding the base to the remaining ingredients either after or prior to the addition of the salicylic acid derivative or at the same time as the addition of the salicylic acid derivative.

A further object of the present invention is the use of the above emulsion for the non-therapeutic treatment of the skin, by topical application.

Another object of the present invention is the use of the above emulsion in order to prevent and/or combat acne and/or greasy skins and/or the ageing and/or pigmentation of the skin, in a non-therapeutic manner.

A further object of the present invention is a method for the cosmetic treatment of the skin in order to combat acne and/or greasy skins and/or the ageing and/or pigmentation of the skin, by applying the emulsion defined above to the skin. The present method may be carried out by topically applying the present emulsion in the same manner and in the same amounts in which conventional compositions containing non-salified salicylic acid derivatives are applied.

Other features of the invention will become apparent in the course of the following descriptions of exemplary embodiments which are given for illustration of the invention and are not intended to be limiting thereof.

EXAMPLES

In the examples, the percentage is given by weight, based on the total weight of the composition. The term "qs 100%" means that that ingredient is present in an amount such that the sum of the amounts of all the ingredients equals 100%.

Example 1

| n-Octanoyl-5-salicylic acid | 5% |
|---|---|
| Lysine | 1 molar equivalent |
| Miglyol 812 | 70% |
| Preserving agents | 0.3% |
| Deionized water | qs 100% |

This emulsion is fairly compact and has a slightly greasy feel. It is in the form of an ointment for treating very dry skin.

Example 2: Anti-ageing Cream for the Face.

| n-Octanoyl-5-salicylic acid | 1.5% |
|---|---|
| Lysine | 1.6% |
| Plant oil | 22% |
| Glyceryl behenate (fatty substance) | 1% |
| Purcellin oil | 2% |
| Liquid fraction of karite butter | 3% |
| Cyclomethicone D5 | 5% |
| Xanthan gum | 0.3% |
| Glycerol | 3% |
| Preserving agents | 0.7% |
| Antioxidant | 0.05% |
| Deionized water | qs 100% |

By applying this light cream to the face daily, the fine wrinkles fade, the complexion becomes shiny and the skin is made smoother during the treatment.

Example 3: Anti-Ageing Cream for the Body.

| n-Octanoyl-5-salicylic acid | 2.5% |
|---|---|
| Lysine | 2.13% |
| Miglyol 812 | 35% |
| Carbomer | 0.75% |
| Preserving agents | 0.3% |
| Deionized water | qs 100% |

When applied daily to the body, this soft cream has lightening and smoothing effects on the skin, which is made very soft by the treatment.

Example 4: Anti-Ageing Cream for the Face.

| n-octanoyl-5-salicylic acid | 1% |
|---|---|
| Lysine | 1.3% |
| N-oleyldihydrosphingosine | 0.1% |
| Apricot almond oil | 20% |
| Liquid fraction of karite butter | 8% |
| Mixture of cetylstearyl 2-ethylhexanoate and isopropyl myristate (90/10) (fatty substance) | 4% |
| Preserving agents | 0.6% |
| Antioxidant | 0.05% |
| Carbomer | 0.75% |
| Xanthan gum | 0.3% |
| Glycerol | 5% |
| Mixture of fatty alcohols (Stearyl/octyldodecanol/behenyl 40/10/50) | 1% |
| Deionized water | qs 100% |

The emulsion of Example 4 according to the present invention was tested for the ageing treatment on a panel of 10 women. The emulsion of Example 4 was considered to be as effective as an emulsion containing non-salified n-octanoyl-5-salicylic acid, all factors being otherwise equal, with, in addition, an absence of irritation.

Moreover, the desquamation caused by the emulsion of Example 4 was tested, in comparison with the same formula containing no lysine, using a paddle turbomixer. The paddle turbomixer makes it possible to measure the spontaneous desquamation. This turbomixer comprises a chamber, and a paddle placed in this chamber. The turbomixer is placed on the sampling surface, for example the arm of the test individual, such that the paddle does not touch this surface; 0.3 ml of a phosphate buffer is introduced into the chamber of the turbomixer, and the paddle is rotated for 1 minute, which stirs the phosphate buffer.

The corneocytes ready to desquamate detach spontaneously from the skin and end up in the phosphate buffer. The buffer containing the corneocytes thus removed is then collected in a glass tube and the tube is centrifuged for 10 minutes at 4,000 rpm. The supernatant is drawn off so as to keep only 1 ml of suspension. The corneocytes are stained (stain =1 volume of 1% basic fuschin +1 volume of 1% crystal violet) and are counted under a microscope. The number of corneocytes counted is greater the more the product applied beforehand to the sampling surface promotes desquamation.

The test is performed at $T_0$ and $T_{24h}$, that is to say at the time of application of the cream and 24 hours after application.

The results of the test are given below and show that the emulsion of Example 4 results in better desquamation than that of the lysine-free emulsion, and thus has a greater keratolytic effect.

TABLE 1

|  | $T_0$ | $T_{24h}$ |
|---|---|---|
| Emulsion of Example 4 | 63.5 | 173.6 |
| Lysine-free emulsion | 60.9 | 67.5 |
| Naked skin | 67.5 | 66.5 |

The results in the table below show the effect of the amount of emulsifying agent of the present invention on the stability of the emulsion. The composition studied is as follows:

|  |  |  |
|---|---|---|
| n-Octanoyl-5-salicylic acid | | x % |
| Lysine | | y % |
| Miglyol 812 | | 34.85% |
| Carbomer | | 0.75% |
| Preserving agents | | 0.7% |
| Deionized water | qs | 100% | x = the amount of n-octanoyl-5-salicylic acid.
y = 1 molar equivalent in order to salify x + that required to neutralize the carbomer.

TABLE 2

| Amount x | Amount y | Result ($T_0$) | Viscosity ($T_0$) | pH ($T_0$) |
|---|---|---|---|---|
| 0.1 | 0.8 | breaks after ¼ hour | — | — |
| 0.5 | 1.03 | fine - some release of oil close to the edges | 72 poises | 5.89 |
| 1 | 1.3 | very fine | 40 poises | 6.07 |
| 1.5 | 1.58 | very fine | 36 poises | 5.82 |
| 2.5 | 2.13 | very fine | 20 poises | 5.83 |
| 5 | 3.51 | very fine - no recrystallization at $T_{15}$ | 8.6 poises | 5.78 |

The expression "very fine" is understood to refer to an emulsion having 0.3 μm to 0.5 μm oil droplets.

From this table, it is observed that the emulsion is stable, is free of n-octanoyl-5-salicylic acid crystals, and has fine, or even very fine, oil droplets dispersed in water for amounts of salicylic acid derivative ranging from 0.1% to 5% by weight, at the initial time $T_0$. For a stability of several days, it is desirable to use from 1% to 5% by weight of the salicylic acid derivative as emulsifying agent.

The inventors have thus indeed found an effective means of stabilizing salicylic acid derivatives, while at the same time removing the irritating side effects of the compositions of the prior art containing these derivatives in acid form. Thus, it is now possible for individuals with sensitive skin to use compositions containing these derivatives in order to combat and/or prevent acne, greasy skin, and the ageing and pigmentation of the skin.

This application is based on French patent application 94-13127 filed on Nov. 3, 1994, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by letters patent of the United States is:

1. A method of stabilizing a dispersion of an oily phase in an aqueous phase, comprising mixing said oily phase and said aqueous phase with a salicylic acid derivative salified with a base, without adding any emulsifying agent, wherein said salicylic acid derivative has the following formula (I):

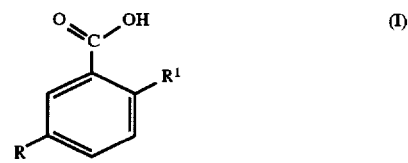

in which;

R represents a saturated, linear or branched aliphatic, alkoxy, alkanoyl, or alkyl carboxy group, each group having 2 to 22 carbon atoms and each optionally substituted with at least one substituent selected from the group consisting of halogen, trifluoromethyl, hydroxyl, hydroxyl esterified with a carboxylic acid having 1 to 6 carbon atoms, carboxyl, and carboxyl esterified with a lower alcohol having 1 to 6 carbon atoms; or an unsaturated, linear or branched alkenyl, alkenyloxy, alkenoyloxy, alkenoyl, or alkenyl carboxy group having one or more conjugated or non-conjugated double bonds, each group having 2 to 22 carbon atoms and each group optionally substituted with at least one substituent selected from the group consisting of halogen, trifluoromethyl, hydroxyl esterified with an carboxylic acid having 1 to 6 carbon atoms, carboxyl, and carboxyl esterified with a lower alcohol having 1 to 6 carbon atoms;

R' represents a hydroxyl group or an ester function of formula:

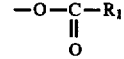

where $R_1$ is saturated or unsaturated aliphatic group having 1 to 18 carbon atoms.

2. The method of claim 1, wherein R is an alkyl or alkoxy radical having 4 to 11 carbon atoms.

3. The method of claim 1, wherein said salicylic acid derivative is n-octanoyl-5-salicylic acid.

4. The method of claim 1, wherein said base is an organic base.

5. The method of claim 1, wherein said base is an amphoteric base.

6. A method of stabilizing a dispersion of an oily phase in an aqueous phase comprising mixing said oily phase and said aqueous phase with a salicylic acid derivative salified with a base, without adding any emulsifying agent;

wherein said base is an amino acid, and wherein said salicylic acid derivative has the following formula (I);

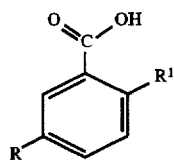

in which;

R represents a saturated, linear or branched aliphatic, alkoxy, alkanoyloxy, alkanoly, or alkyl carboxy group, each group having 2 to 22 carbon atoms and each groups optionally substituted with at least one substituent selected from the group consisting of halogen, trifluoromethyl, hydroxyl, hydroxyl esterified with a carboxylic acid having 1 to 6 carbon atoms, carboxyl, and carboxyl esterified with a lower alcohol having 1 to 6 carbon atoms; or an unsaturated, linear or branches alkenyl, alkenyloxy, alkenoyloxy, alkenoyl, or alkenyl carboxy group having one or more conjugated or non-conjugated double bonds, each group having 2 to 22 carbon atoms and each group optionally substituted with at least one substituted selected from the group consisting of halogen, trifluoromethyl, hydroxyl, hydroxyl esterified with an carboxylic acid having 1 to 6 carbon atoms, carboxyl, and carboxyl esterified with a lower alcohol having 1 to 6 carbon atoms;

R' represents a hydroxyl group or an ester function of formula;

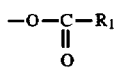

where $R_1$ is a saturated or unsaturated aliphatic group having 1 to 18 carbon atoms.

7. A of stabilizing a dispersion of an oily phase in an aqueous phase comprising mixing said oily phase and said aqueous phase with a salicylic acid derivative salified with a base, without adding any emulsifying agent; and said base is selected from the group consisting of arginine and lysine, and wherein said salicylic acid derivative has the following formula (I);

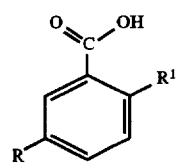

in which;

R represents a saturated, linear or branched aliphatic, alkoxy, alkanoyloxy, alkanoyl, or alkyl carboxy group, each group having 2 to 22 carbon atoms and each group optionally substituted with at least one substituent selected from the group consisting of halogen, trifluoromethyl, hydroxyl, hydroxyl esterified with a carboxylic acid having 1 to 6 carbon atoms, carboxyl, and carboxyl esterified with a lower alcohol having 1 to 6 carbon atoms; or unsaturated, linear or branched alkenyl, alkenyloxy, alkenoyloxy, alkenoyl, or alkenyl carboxy group having one or more conjugated or non-conjugated double bonds, each group having 2 to 22 carbon atoms and each group optionally substituted with al least one substituent selected from the group consisting of halogen, trifluoromethyl, hydroxyl, hydroxyl esterified with an carboxylic acid having 1 to 6 carbon atoms, carboxyl, and carboxyl esterified with a lower alcohol having 1 to 6 carbon atoms;

R' represents a hydroxyl group or an ester function of formula:

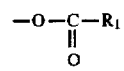

where $R_1$ is a saturated or unsaturated aliphatic group having 1 to 18 carbon atoms.

8. A cosmetic and/or dermatological emulsion, free of emulsifying agent comprising:
(a) an oil phase;
(b) an aqueous phase; and
(c) at least one salicylic acid derivative of formula (I) below, salified with a base:

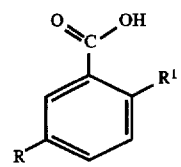

in which:

R represents a saturated linear or branched aliphatic, alkoxy, alkanoyloxy, alkanoyl, or alkyl carboxy group, each group having 2 to 22 carbon atoms and each group optionally substituted with at least one substituent selected from the group consisting of halogen, trifluoromethyl, hydroxyl, hydroxyl esterified with a carboxylic acid having 1 to 6 carbon atoms, carboxyl, and carboxyl esterified with a lower alcohol having 1 to 6 carbon atoms; or an unsaturated, linear or branched alkenyl, alkenyloxy, alkenoyloxy, alkenoyl, or alkenyl carboxy group having one or more conjugated or non-conjugated double bonds, each group having 2 to 22 carbon atoms and each group optionally substituted with at least one substituent selected from the group consisting of halogen, trifluoromethyl, hydroxyl, hydroxyl esterified with a carboxylic acid having 1 to 6 carbon atoms, carboxyl, and carboxyl esterified with a lower alcohol having 1 to 6 carbon atoms;

R' represents a hydroxyl group or an ester function of formula:

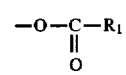

wherein $R_1$ is a saturated or unsaturated aliphatic group having 1 to 18 carbon atoms.

wherein at least a portion of said salicylic acid derivative is at the oil-water interface.

9. The emulsion of claim 8, wherein R is an alkyl or alkoxy radical having 4 to 11 carbon atoms.

10. The emulsion of claim 8, wherein said salicylic acid derivative is n-octanoyl-5-salicylic acid.

11. The emulsion of claim 8, wherein said base is an organic base.

12. The emulsion of claim 8, wherein said base is an amphoteric base.

13. A cosmetic and/or dermatological emulsion, comprising:

(a) an oil phase;

(b) an aqueous phase; and (c) at least one salicylic acid derivative of formula (I) below, salified with a base:

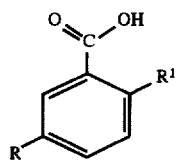
(I)

in which:

R represents a saturated, linear or branched aliphatic, alkoxy, alkanoyloxy, alkanoyl, or alkyl carboxy group, each group having 2 to 22 carbon atoms and each group optionally substituted with at least one substituent selected from the group consisting of halogen, trifluoromethyl, hydroxyl, hydroxyl esterified with a carboxylic acid having 1 to 6 carbon atoms, carboxyl, and carboxyl esterified with a lower alcohol having 1 to 6 carbon atoms; or an unsaturated, linear, or branched alkenyl, alkenyloxy, alkenoyloxy, alkenoyl, or alkenyl carboxy group having one or more conjugated or non-conjugated double bonds, each group having 2 to 22 carbon atoms and each group optionally substituted with at least one substituent selected from the group consisting of halogen, trifluoromethyl, hydroxyl, hydroxyl esterified with a carboxylic acid having 1 to 6 carbon atoms, carboxyl, and carboxyl esterified with a lower alcohol having 1 to 6 carbon atoms;

R' represents a hydroxyl group or an ester function of formula:

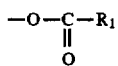

wherein $R_1$ is a saturated or unsaturated aliphatic group having 1 to 18 carbon atoms, wherein at least a portion of said salicylic acid derivative is at the oil-water interface; and said base is an amino acid without an emulsifying agent added there to.

14. A cosmetic and/or dermatological emulsion, comprising:

(a) an oil phase;

(b) an aqueous phase; and (c) at least one salicylic acid derivative of formula (I) below, salified with a base:

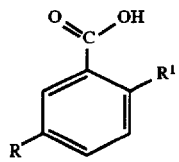
(I)

in which:

R represents a saturated, linear or branched aliphatic, alkoxy, alkanoyloxy, alkanoyl, or alkyl carboxy group, each group having 2 to 22 carbon atoms and each group optionally substituted with at least one substituent selected from the group consisting of halogen, trifluoromethyl, hydroxyl, hydroxyl esterified with a carboxylic acid having 1 to 6 carbon atoms, carboxyl, and carboxyl esterified with a lower alcohol having 1 to 6 carbon atoms; or an unsaturated, linear, or branched alkenyl, alkenyloxy, alkenoyloxy, alkenoyl, or alkenyl carboxy group having one or more conjugated or non-conjugated double bonds, each group having 2 to 22 carbon atoms and each group optionally substituted with at least one substituent selected from the group consisting of halogen, trifluoromethyl, hydroxyl, hydroxyl esterified with a carboxylic acid having 1 to 6 carbon atoms, carboxyl, and carboxyl esterified with a lower alcohol having 1 to 6 carbon atoms;

R' represents a hydroxyl group or an ester function of formula:

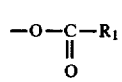

wherein $R_1$ is a saturated or unsaturated aliphatic group having 1 to 18 carbon atoms, wherein at least a portion of said salicylic acid derivative is at the oil-water interface; and said base is selected from the group consisting of arginine and lysine without an emulsifying agent added there to.

15. The emulsion of claim 8, wherein said salicylic acid derivative is present in an amount of from 0.5% to 10% by weight, based on the total weight of the emulsion.

16. The emulsion of claim 8, which comprises at least one polar oil.

17. The emulsion of claim 16, wherein said oil is present in an amount of from 10% to 70% by weight, based on the total weight of the emulsion.

18. The emulsion of claim 8, further comprising an adjuvant selected from the group consisting of ceramides, pseudoceramides, glycoceramides, and essential fatty acids.

19. The emulsion of claim 8, further comprising at least one gelling agent.

20. A cosmetic and/or dermatological emulsion, comprising:

(a) an oil phase;

(b) an aqueous phase; and (c) at least one salicylic acid derivative of formula (I) below, salified with lysine or arginine:

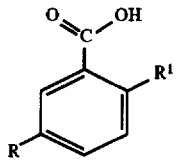
(I)

in which:

R represents a saturated, linear or branched aliphatic, alkoxy, alkanoyloxy, alkanoyl, or alkyl carboxy group, each group having 2 to 22 carbon atoms and each group optionally substituted with at least one substituent selected from the group consisting of halogen, trifluoromethyl, hydroxyl, hydroxyl esterified with a carboxylic acid having 1 to 6 carbon atoms, carboxyl, and carboxyl esterified with a lower alcohol having 1 to 6 carbon atoms; or an unsaturated, linear or branched alkenyl, alkenyloxy, alkenoyloxy, alkenoyl, or alkenyl carboxy group having one or more conjugated or non-conjugated double bonds, each group having 2 to 22 carbon atoms and each group optionally substituted with at least one substituent selected from the group consisting of halogen, trifluoromethyl, hydroxyl, hydroxyl esterified with a carboxylic acid having 1 to 6 carbon atoms, carboxyl, and carboxyl esterified with a lower alcohol having 1 to 6 carbon atoms;

R' represents a hydroxyl group or an ester function of formula:

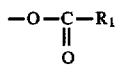

wherein $R_1$ is a saturated or unsaturated aliphatic group having 1 to 18 carbon atoms; and at least a portion of said salicylic acid derivative is at the oil-water interface without an emulsifying agent added there to.

21. A method for treating or combating acne, greasy skin, the ageing, pigmentation and combinations thereof of the skin, comprising applying an emulsion to the skin, said emulsion comprising:

(a) an oil phase;
(b) an aqueous phase; and
(c) at least one salicylic acid derivative of formula (I) below, salified with a base:

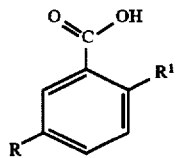

(I)

in which:

R represents a saturated, linear or branched aliphatic, alkoxy, alkanoyloxy, alkanoyl, or alkyl carboxy group, each group having 2 to 22 carbon atoms and each group optionally substituted with at least one substituent selected from the group consisting of halogen, trifluoromethyl, hydroxyl, hydroxyl esterified with a carboxylic acid having 1 to 6 carbon atoms, carboxyl, and carboxyl esterified with a lower alcohol having 1 to 6 carbon atoms; or an unsaturated, linear or branched alkenyl, alkenyloxy, alkenoyloxy, alkenoyl, or alkenyl carboxy group having one or more conjugated or non-conjugated double bonds, each group having 2 to 22 carbon atoms and each group optionally substituted with at least one substituent selected from the group consisting of halogen, trifluoromethyl, hydroxyl, hydroxyl esterified with a carboxylic acid having 1 to 6 carbon atoms, carboxyl, and carboxyl esterified with a lower alcohol having 1 to 6 carbon atoms;

R' represents a hydroxyl group or an ester function of formula:

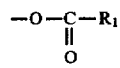

wherein $R_1$ is a saturated or unsaturated aliphatic group having 1 to 18 carbon atoms, wherein at least a portion of said salicylic acid derivative is at the oil-water interface without an emulsifying agent added there to.

22. The method of claim 1 wherein said dispersion further comprises at least one gelling agent selected from the group consisting of clays, polysaccharide gums (xanthan), carboxyvinyl polymers and carbomers.

23. The method of claim 1 wherein said dispersion further comprises at least one lipophilic or hydrophilic active agent selected from the group consisting of moisturizing or cicatrizing agents, β-hydroxy acids, α-hydroxy acids, hydrophilic or lipophilic screening agents and dermatological active agents.

* * * * *